United States Patent
Akonur et al.

(10) Patent No.: US 8,521,482 B2
(45) Date of Patent: Aug. 27, 2013

(54) SIMULATION OF PATIENT DRAIN PHASE IN PERITONEAL DIALYSIS

(75) Inventors: Alp Akonur, Evanston, IL (US); Ying-Cheng Lo, Green Oaks, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1225 days.

(21) Appl. No.: 12/389,886

(22) Filed: Feb. 20, 2009

(65) Prior Publication Data

US 2010/0217180 A1    Aug. 26, 2010

(51) Int. Cl.
*G06F 7/60*    (2006.01)

(52) U.S. Cl.
USPC ............................................................ 703/2

(58) Field of Classification Search
USPC ............................................................ 703/2
See application file for complete search history.

(56) References Cited

U.S. PATENT DOCUMENTS

| | | | |
|---|---|---|---|
| 5,334,139 A | 8/1994 | Jeppsson et al. | |
| 5,643,201 A | 7/1997 | Peabody et al. | |
| 5,670,057 A * | 9/1997 | Chen et al. | 210/739 |
| 6,074,359 A | 6/2000 | Keshaviah et al. | |
| 6,558,343 B1 | 5/2003 | Neftel | |
| 6,592,542 B2 * | 7/2003 | Childers et al. | 604/29 |
| 6,976,973 B1 | 12/2005 | Ruddell et al. | |
| 7,238,164 B2 | 7/2007 | Childers et al. | |
| 2008/0161751 A1 * | 7/2008 | Plahey et al. | 604/29 |
| 2009/0271119 A1 * | 10/2009 | Hamada et al. | 702/19 |
| 2010/0010427 A1 | 1/2010 | Yu et al. | |

FOREIGN PATENT DOCUMENTS

WO    2005/035023    4/2005

OTHER PUBLICATIONS

M. Misra, K.D. Nolph, "Adequacy in dialysis: intermittent versus continuous therapies" Nefrologia. vol. XX. Suplemento 3. 2000, pp. 25-32.*
International Search Report and Written Opinion for International Application No. PCT/US2010/024745 mailed on Jun. 21, 2010.
Kazuo Kumano, "Minimizing the drainage period for continuous ambulatory peritoneal dialysis," Peritoneal Dialysis International, Pergamon Press, New York, NY, US, vol. 14, Jan. 1, 1994, pp. 52-55.
James C. Brandes, et al., "Optimization of Dialysate Flow and Mass Transfer During Automated Peritoneal Dialysis," American Journal of Kidney Diseases, vol. 25, No. 4, Apr. 1995, 9 pages.
Bengt Rippe, et al., "Computer simulations of peritoneal fluid transport in CAPD," Kidney International, vol. 40, (1991), pp. 315-325.
Edward Vonesh, et al., "Net Fluid Absorption Membrane Transport Models of Peritoneal Dialysis," Blood Purif., 1992, vol. 10, pp. 209-226.
International Preliminary Report on Patentability for International Application No. PCT/US2010/024745 mailed on May 5, 2011.

* cited by examiner

*Primary Examiner* — Dwin M Craig
(74) *Attorney, Agent, or Firm* — K&L Gates LLP (57) ABSTRACT

A method of modeling a patient's peritoneal dialysis drain phase includes (i) modeling a first segment of a drain phase curve as having a constant flowrate; (ii) modeling a second segment of a drain phase curve as having a decaying exponential flowrate; and (iii) incorporating a switching component into the first and second components so that (a) at a first time the first segment is active and while the second segment is inactive and (b) at a second time the first segment is inactive and while the second segment is active.

21 Claims, 7 Drawing Sheets

| MDP | 85 | % |
|---|---|---|
| FRT | 75 | ml/min |
| Flow Trans | 75 | % |
| Q max | 80 | ml/min |

FIG. 6B

| PET Characteristic | Cycle | UF per Exchange (ml) | Residual Volume (ml) | Drain Time (min) | Drained Volume (ml) | Volume Infused (ml) | Peak Volume (ml) | Dwell Time (min) |
|---|---|---|---|---|---|---|---|---|
| H | 1 | 139 | 150 | 22.5 | 1753 | 2000 | 2289 | 112 |
| | 2 | 129 | 537 | 26.0 | 2035 | 2000 | 2666 | 109 |
| | 3 | 128 | 631 | 26.9 | 2105 | 2000 | 2758 | 108 |
| | 4 | 128 | 654 | 27.1 | 2122 | 2000 | 2781 | 107 |

FIG. 6C

| Net UF per Period (ml) | Final Urea Clearance (ml/min) | Cum Weekly Urea Kt/V per Period | Cum Weekly Ccr (L/week/1.73) per period | Cum Daily B2-M Clearance per Period (ml/min) | Grams Glucose Absorbed per Exchange |
|---|---|---|---|---|---|
| 524 | 15.79 | 1.19 | 38.70 | 0.53 | 27.16 |

| MDP | 85 | % |
|---|---|---|
| FRT | 75 | ml/min |
| Flow Trans | 65 | % |
| Q max | 80 | ml/min |

FIG. 8B

| PET Characteristic | Cycle | UF per Exchange (ml) | Residual Volume (ml) | Drain Time (min) | Drained Volume (ml) | Volume Infused (ml) | Peak Volume (ml) | Dwell Time (min) |
|---|---|---|---|---|---|---|---|---|
| H | 1 | 129 | 150 | 24.2 | 1700 | 2000 | 2278 | 83 |
| | 2 | 98 | 579 | 18.7 | 1459 | 1500 | 2177 | 89 |
| | 3 | 90 | 718 | 19.8 | 1544 | 1500 | 2308 | 88 |
| | 4 | 89 | 764 | 20.1 | 1573 | 1500 | 2352 | 87 |
| | 5 | 89 | 780 | 20.2 | 1583 | 1500 | 2368 | 87 |

FIG. 8C

| Net UF per Period (ml) | Final Urea Clearance (ml/min) | Cum Weekly Urea Kt/V per Period | Cum Weekly Ccr (L/week/1.73) per period | Cum Daily B2-M Clearance per Period (ml/min) | Grams Glucose Absorbed per Exchange |
|---|---|---|---|---|---|
| 494 | 15.72 | 1.18 | 38.36 | 0.55 | 21.58 |

# SIMULATION OF PATIENT DRAIN PHASE IN PERITONEAL DIALYSIS

BACKGROUND

The present disclosure relates to medical fluid delivery and in particular to peritoneal dialysis fluid delivery.

Due to disease or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

One type of dialysis is peritoneal dialysis. Peritoneal dialysis uses a dialysis solution or "dialysate", which is infused into a patient's peritoneal cavity through a catheter implanted in the cavity. The dialysate contacts the patient's peritoneal membrane in the peritoneal cavity. Waste, toxins and excess water pass from the patient's bloodstream through the peritoneal membrane and into the dialysate. The transfer of waste, toxins, and water from the bloodstream into the dialysate occurs due to diffusion and osmosis, i.e., an osmotic gradient occurs across the membrane. The spent dialysate drains from the patient's peritoneal cavity and removes the waste, toxins and excess water from the patient. This cycle is repeated.

There are various types of peritoneal dialysis therapies, including continuous ambulatory peritoneal dialysis ("CAPD") and automated peritoneal dialysis ("APD"). CAPD is a manual dialysis treatment, in which the patient connects an implanted catheter to a drain and allows a spent dialysate fluid to drain from the patient's peritoneal cavity. The patient then connects the catheter to a bag of fresh dialysate and manually infuses fresh dialysate through the catheter and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient repeats the manual dialysis procedure.

In CAPD the patient performs several drain, fill, and dwell cycles during the day, for example, about four times per day. Each treatment cycle typically takes about four to five hours. APD is similar to CAPD in that the dialysis treatment includes a drain, fill, and dwell cycle. APD machines, however, perform four to five cycles of peritoneal dialysis treatment automatically, typically overnight while the patient sleeps. Like CAPD, APD machines connect fluidly to an implanted catheter, to one or more sources or bags of fresh dialysate and to a fluid drain.

The APD machines pump fresh dialysate from the dialysate source, through the catheter, into the patient's peritoneal cavity and allow the dialysate to dwell within the cavity so that the transfer of waste, toxins and excess water from the patient's bloodstream to the dialysate solution can take place. The APD machines then pump spent dialysate from the peritoneal cavity, though the catheter, to the drain. APD machines are typically computer controlled so that the dialysis treatment occurs automatically when the patient is connected to the dialysis machine, for example, when the patient sleeps. That is, the APD systems automatically and sequentially pump fluid into the peritoneal cavity, allow for a dwell, pump fluid out of the peritoneal cavity and repeat the procedure. As with the manual process, several drain, fill, and dwell cycles will occur during APD. A "last fill" is typically used at the end of APD, which remains in the peritoneal cavity of the patient when the patient disconnects from the dialysis machine for the day.

In both CAPD and APD, the therapy must allow for a certain amount of time for the patient drain phase. It is important that the drain phase be sufficiently long to allow the patient to drain as completely as possible. On the other hand, if too much time is allowed for the drain phase, that is, the patient is basically finished draining too far in advance of the end of the drain phase, then the drain phase is extending needlessly into time that the patient could be filling or is appending the last fill's dwell phase needlessly. A need accordingly exists for a way to predict and optimize drain phase time to allow for the patient to drain completely or as much as is reasonably possible without needlessly extending drain time and wasting time that could be used to increase therapy dwell.

SUMMARY

The present disclosure sets forth a method and apparatus for predicting a patient's optimal drain phase time. The optimal drain phase time is useful for at least two purposes. First, the optimal drain phase time can be implemented into the patient's continuous ambulatory peritoneal dialysis ("CAPD") or automated peritoneal dialysis ("APD") treatment. Second, the optimal drain phase time can be used in the further modeling of possible treatments or therapy regimes for the patient, one or more desirable ones of which can then be selected for actual use. The further treatment or prescription modeling can be done using a three-pore model as discussed below.

The drain phase modeling attempts to match the patient's actual drain profile given certain inputs. One important patient specific input is maximum drain flowrate or $Q_{max}$. $Q_{max}$ typically occurs at the start of the drain. Some patients will drain more quickly than others due to patient-specific physical characteristics. Also, the position of the patient affects $Q_{max}$. A patient standing or sitting may drain quicker than if the same patient is lying down in a supine or prone position. $Q_{max}$ is determined in one embodiment by experimentation with the patient in a drain position that the patient expects to be for at least most treatments.

Figure 1:
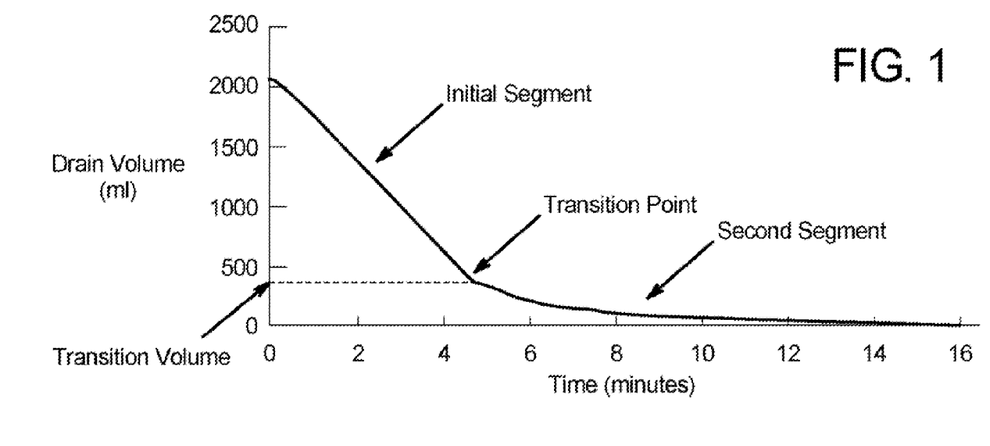
FIGS. 1 and 2 are drain volume and drain phase flowrate profiles derived from actual patient data via a study.
Figure 2:
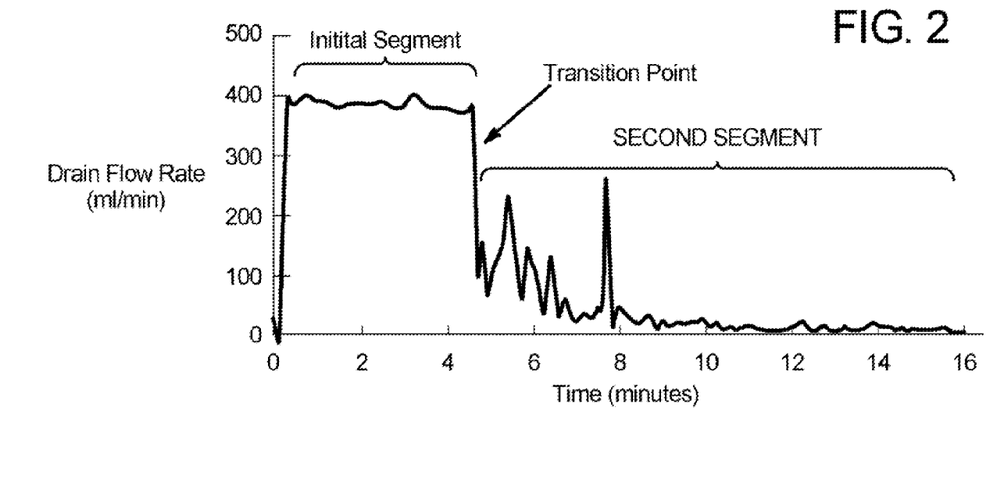

Referring now to the drawings and in particular to FIGS. 1 and 2, typical drain volume and corresponding flowrate profiles, respectively, are shown. The profiles were derived in a study by Brandes J. C., Packard, J. W., Watters S. K., Fritsche C., *Optimization of Dialysate Flow and Mass Transfer During Automated Peritoneal Dialysis, American Journal of Kidney Diseases*, Vol. 25, No. 4 (April), 1995, pp. 603-610. FIG. 1 shows a constant drop in drain volume from a full volume of about 2000 ml to a transition drain volume of about 350 to 400 ml. This constant drop occurs while flowrate is generally at a maximum, e.g., $Q_{max}$, which is about 350 ml/min as seen in FIG. 2. Below the transition volume, the volume drains according to a decaying exponential curve. Drain flowrate after the transition point also slows to zero according to a similar curve. The transition point in both FIGS. 1 and 2 separates a first segment from a second segment as discussed in detail below.

According to the present method and apparatus, an equation has been formed that models the first and second segments. The equation relies principally on $Q_{max}$ for the first segment. The equation employs a switching component $\Phi$ that either (i) switches the first segment portion of the equation on and the second segment portion of the equation off or (ii) switches the first segment portion of the equation off and the second segment portion of the equation on. The transition time (or volume) at which switching component $\Phi$ switches from 1 to 0 is determined empirically, e.g., the duration of the constant high flow Qmax can be measured for each individual patient, and for a particular drain position. The second segment portion of the equation also employs an exponential drain rate constant $\alpha$, which is patient specific and is determined empirically. The equation relies principally on a for the second segment.

The drain modeling equation can be used in a number of ways. First, it can be used to form individual settings for flowrate threshold ("FRT") and/or minimum drain volume ("MDV"). One or both of FRT and MDV may be set as alarm limits in an automated peritoneal dialysis ("APD") machine (which can use either gravity draining or pumped draining).

Second, the drain modeling equation can be used to more accurately model a patient's reaction to therapy, e.g., via a three-pore model. For example, the three-pore model uses a drain time (or dwell time, which is a function of drain time) in one or more places to model a particular patient's reaction to a particular therapy prescription.

Third, the drain modeling equation can be used to set drain and dwell times or periods for actual operation of an APD machine, for example, performing a multiple exchange therapy. Again, the machine can be a gravity drain machine or drain via a pump.

Fourth, the drain modeling equation can be used to set drain times or periods for patients performing manual peritoneal dialysis or CAPD.

It is accordingly an advantage of the present disclosure to provide a method and apparatus that attempt to optimize a drain phase in peritoneal dialysis.

It is another advantage of the present disclosure to provide a method and apparatus that attempt to minimize drain time.

It is a further advantage of the present disclosure to provide a method and apparatus that attempt to maximize drain volume.

It is yet another advantage of the present disclosure to provide a method and apparatus that attempt to prevent patient overfill.

It is yet a further advantage of the present disclosure to provide a method and apparatus that attempt to prevent low drain flowrate alarms.

It is still another advantage of the present disclosure to provide a method and apparatus that attempt to improve estimation of therapy outcome parameters such as UF, urea clearance and creatinine clearance.

Additional features and advantages are described herein, and will be apparent from the following Detailed Description and the figures.

DETAILED DESCRIPTION

The drain volume modeling method and apparatus of the present disclosure uses the concepts and terminology described below.

Maximum drain flowrate, $Q_{max}$, is the initial drain flowrate, which should be a maximum flowrate of the drain flowrate profile. The present disclosure applies to different kinds of APD machines. For example, the APD machine can use a gravity fill and drain, in which the supply bag is placed elevationally above the patient and the drain bag is placed elevationally below the patient. For such a machine, $Q_{max}$ is determined empirically as discussed below. $Q_{max}$ is also determined empirically for continuous ambulatory peritoneal dialysis ("CAPD"), which also uses gravity for filling and draining. The HomeChoice® machine, made by the assignee of the present disclosure, pumps spent fluid from the patient to drain. Here, $Q_{max}$ is set by the pump speed, does not need to be determined empirically, and is independent of the patient's drain position.

For modeling purposes, $Q_{max}$ is assumed to remain constant until the patient drain transitions to an exponential decay portion or segment of the profile. $Q_{max}$ is patient specific and is also patient drain position specific. $Q_{max}$ is determined empirically by, for example, weighing the patient's drain over time for a number of exchanges and then averaging the resulting rate. $Q_{max}$ may vary for a patient depending upon whether the patient is sitting, laying down or standing during drain. It is contemplated therefore to obtain empirical data for $Q_{max}$ while the patient is positioned for drain in a position that the patient intends to be for most or all drains. It is also contemplated to obtain empirical data for $Q_{max}$ while the patient is in different positions for drain, e.g., one set of data while the patient is standing for drain, one set of data while the patient is sitting for drain, and a third set of data while the patient is laying down for drain. In such case, an automated peritoneal dialysis ("APD") machine can be programmed to ask the patient which drain position the patient intends to use for the current treatment.

Flow transition percent ("FTP") is the percentage of the peritoneal volume at which the patient drain transitions from the first segment, having constant drain flowrate $Q_{max}$, to the second segment having the decaying exponential flowrate. FTP sets the volume (or percentage of total time) at which switching component $\Phi$, discussed in detail herein, switches from 1 to 0. FTP is patient specific and is determined empirically regardless of the type of APD machine (gravity drain or pump to drain) used. FTP may also be dependent upon patient drain position for gravity fed systems or treatments.

The second drain profile segment, having the decaying exponential flowrate, is controlled in large part by a decaying exponential constant $\alpha$, which is also patient specific and is determined empirically regardless of the type of APD machine (gravity drain or pump to drain) used or if CAPD is performed instead. α itself may depend on drain type, pump or gravity, and perhaps pump type, e.g., peristaltic versus membrane. α may also be dependent upon patient drain position for gravity fed systems or treatments. α is determined by obtaining multiple data points (volume for a given time and flowrate for a given time) during the second or decaying exponential drain flow and volume segment. Different "potential" values of a are then plugged into the second segment of the drain model shown below until a value of α that outputs correct volume and correct flowrate values for the corresponding points in time, or which best match the measured data, is obtained. α can for example be in a range of 0.1 to 0.15.

One parameter that may be set in the software of an APD machine for alarm purposes is a minimum drain percentage ("MDP"). MDP sets a drain limit above which the patient's drain volume must reach during the drain phase. If, for example, the patient does not drain at least eighty percent of the total spent volume in the patient's peritoneum, The APD will sound an alarm and therapy may be halted, preventing the machine from advancing to the next fill phase until the low drain is addressed. As discussed below, MDP can be used with the modeled drain profiles to determine an appropriate dwell time for the patient, in particular, it sets a minimum dwell time to reach MDP Flowrate threshold ("FRT") may also be set in the software of an APD machine for alarm purposes. FRT sets a minimum drain flowrate level below which the machine may alarm, for example, indicating that the drain flowrate is so low that the treatment in essence is wasting time by continuing drain. FRT can alternatively be set to define a drain flow limit below which the drain is stopped. As discussed below, FTP and MDP can be used, alone or in combination, with the modeled drain profiles to determine an appropriate dwell time for the patient, which ensures that the dwell time is long enough for MDP to be met but does not continue long enough for the drain flowrate to fall below FTP.

Figure 3:
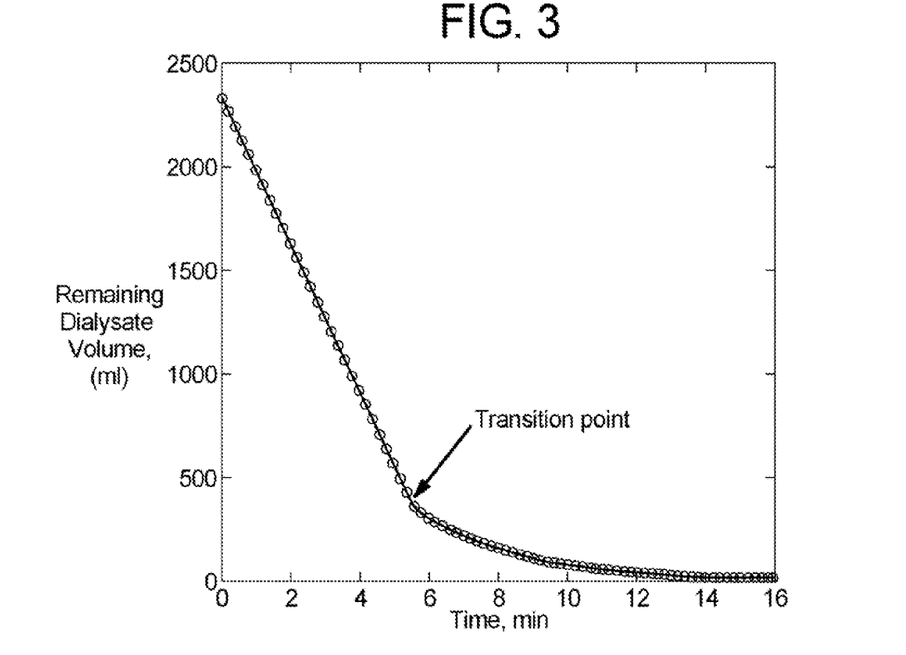
FIGS. 3 and 4 are drain volume and drain phase flowrate profiles derived via the modeling method and apparatus of the present disclosure.
Figure 4:
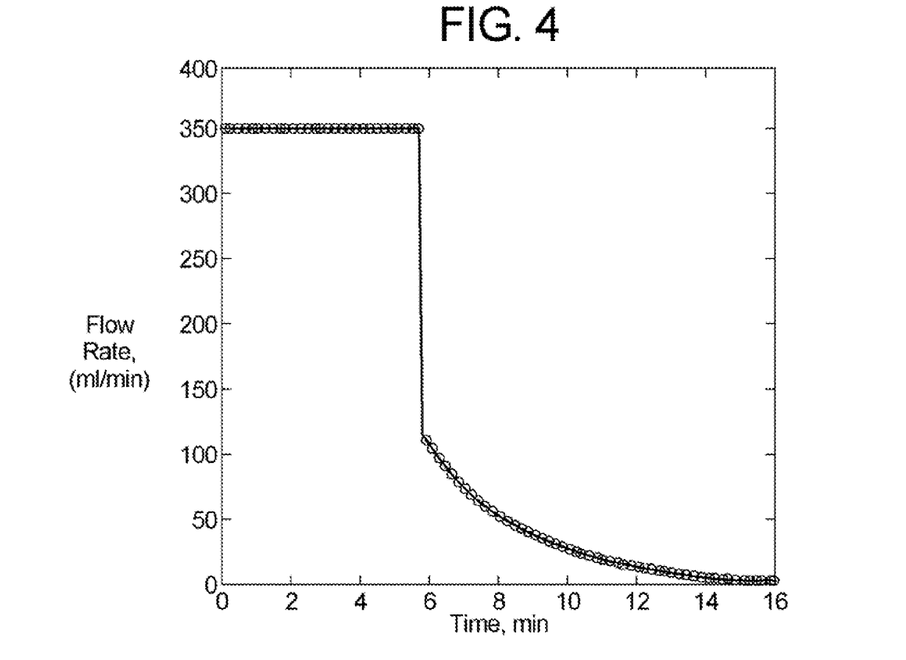

Referring now to FIGS. 3 and 4, drain volume and drain flowrate profiles are shown, respectively, which have been modeled to attempt to match the actual drain volume and drain flowrate profiles of FIGS. 1 and 2. The drain volume profile of FIG. 3 is obtained via the following equation or algorithm:

$$V_D = [V_{D0} - Q_{max}*t]*\Phi + [V_{D0}*e^{-\alpha t}]*(1-\Phi), \text{ wherein}$$

$V_D$ is an instantaneous remaining drain volume in the patient at time t $V_{D0}$ is an initial patient drain volume (fill volume plus UF accumulated over previous dwell);

$Q_{max}$ discussed above is a starting flowrate and is assumed to be constant;

$\Phi$ discussed above is a switching component (from 1 to 0 at FTP), which is based on time or volume;

α discussed above is a decaying exponential constant; and t is time.

The modeled flowrate profile of FIG. 4 is determined by dividing a change in volume by a corresponding change in time, e.g., drop from 2300 ml to 1600 ml over first two minutes leading to flowrate over that period of 350 m/min. Specific flowrate values can be obtained via a derivative dV/dT, especially in the second, non-linear, segment.

The equation above and resulting profiles of FIGS. 3 and 4 show a first segment that is dependent on $V_{D0}$ and $Q_{max}$. $V_{D0}$ is the previous fill volume plus an amount of ultrafiltrate ("UF") removed from the patient over the last dwell. The amount of UF can be estimated via a three-pore model given certain parameters, such as patient physiological characteristics (ability to remove UF), dextrose level of dialysate used and dwell time. For example, if the patient fill is 2000 ml of fresh dialysate and it is determined from a patient kinetic model, such as a three-pore model, or perhaps experimentally, that the patient will acquire 300 ml of ultrafiltrate over the course of a known dwell period, $V_{D0}$ will be set to 2300 ml. $Q_{max}$ is determined empirically or set via pump speed.

The equation above and resulting profiles of FIGS. 3 and 4 show a second segment that is dependent on $V_{D0}$ and α. α is determined empirically as discussed above. The transition point in the above equation occurs when $\Phi$ switches from 1 to 0, which is determined empirically. The corresponding transition point in the profiles of FIGS. 3 and 4 occurs when the straight line transitions to the curved or exponentially decaying line.

Figure 5:
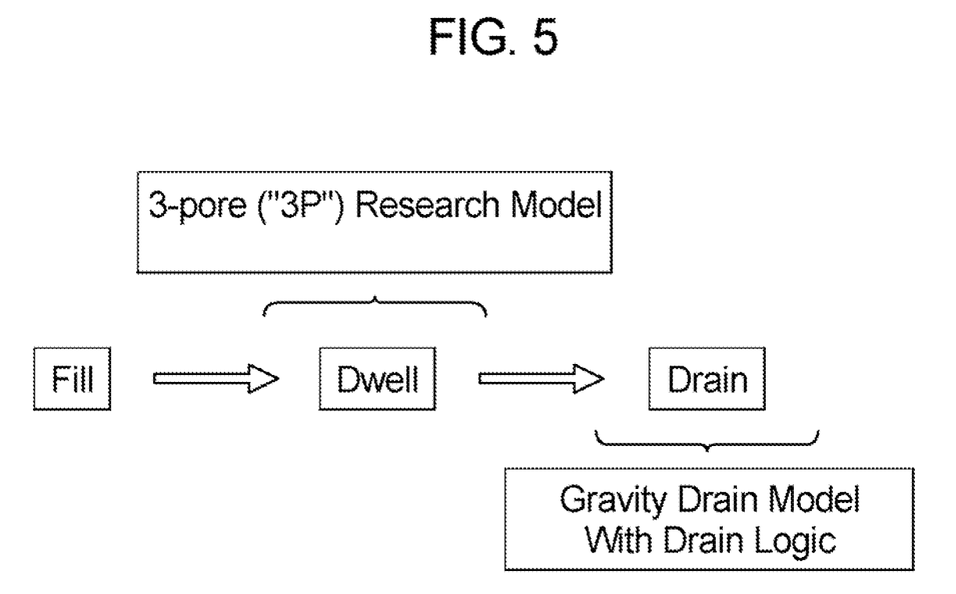
FIG. 5 is a schematic diagram illustrating how the drain volume modeling method and apparatus of the present disclosure is used with kinetic modeling of patient therapy outcomes, e.g., using a three-pore model.

Referring now to FIG. 5, a schematic showing fill, dwell and drain phases of a peritoneal dialysis treatment illustrates how the drain volume modeling method and apparatus of the present disclosure interfaces with the kinetic modeling of patient therapy outcomes, e.g., using a three-pore model. The duration of the fill phase in APD is set via a pump speed. The duration of the fill phase in CAPD is determined principally by head height of the fill bag above the patient.

Dwell phase duration and drain phase duration are related. A treatment typically requires multiple, e.g., four, fills that are made over an entire treatment, e.g., eight hours. The set fill times leave only so much time for the dwell and drain phases. The less time needed for drain, the more time left for dwell, which is desirable from both clearance and UF standpoints.

Further, accurately modeling an adequate (MDP satisfied) but efficient (FTP satisfied) allows the dwell phase times to be determined accurately given the set fill times. The dwell phase times are important to the kinetic modeling as seen in FIG. 5. Thus, determining accurate dwell times allows the kinetic modeling of patient results to different therapy prescriptions to be done more accurately. One suitable modified three-pore kinetic model is described in Rippe B., Sterlin G., and Haraldsson B., *Computer Simulations of Peritoneal Fluid Transport in CAPD*, Kidney Int. 1991; 40: 315 to 325. Another suitable modified three-pore kinetic model is described in Vonesh E. F. and Rippe B., *Net Fluid Adsorption Under Membrane Transport Models of Peritoneal Dialysis*, Blood Purif. 1992; 10: 209 to 226, the entire contents of each of which are incorporated herein by reference and relied upon.

Figure 6A:
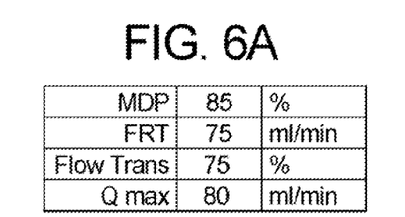
FIGS. 6A to 6C illustrate a first therapy modeled via kinetic model using information obtained from the drain volume modeling method and apparatus of the present disclosure.
Figure 6B:
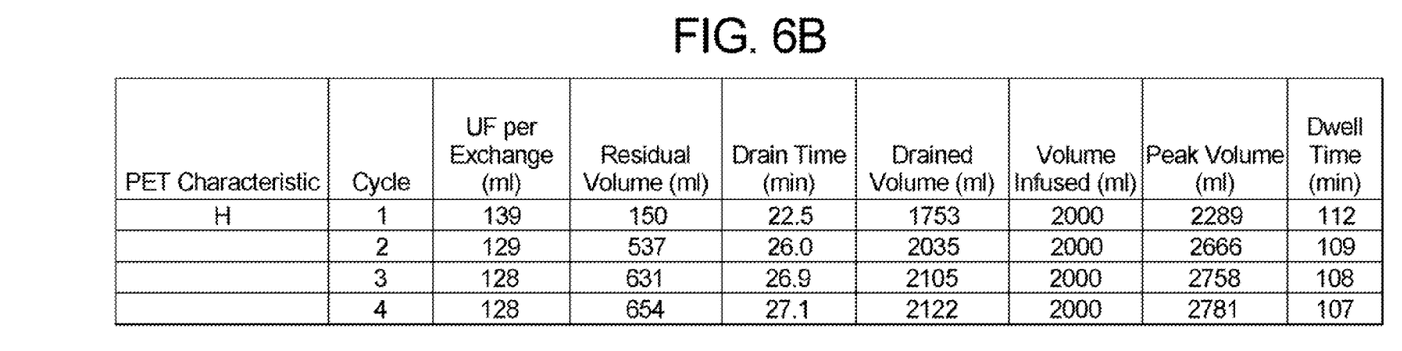
Figure 6C:
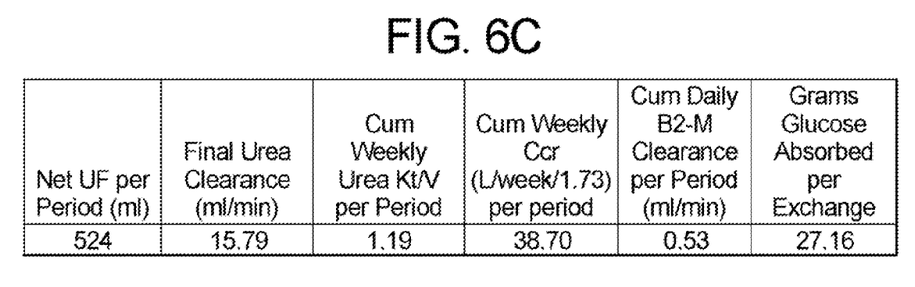

Referring now to FIGS. 6A to 6C, one example therapy modeled using a three-pore kinetic model is illustrated. The three-pore kinetic model used drain times selected from drain volume and drain flowrate profiles, similar to FIGS. 3 and 4, which were determined via the equation above. Here, the patient undergoes four exchanges of two liter fills each, totaling eight liters. PET characteristic is H or high meaning the patient in general has high toxin and glucose clearances.

A modeled drain time and corresponding drain volume is shown for each cycle in FIG. 6B. In each case, the drain volume met the MDP requirement of 85%, and the minimum drain flowrate met the FRT requirement of 75 ml/min, both of which are shown in FIG. 6A. FIG. 6A also shows patient specific parameters, namely, an FTP of 75% (percentage of drain after which switching component $\Phi$ changes from 1 to 0) and a $Q_{max}$ of 80 ml/min.

As seen in FIG. 6B, the drain time and drain volume selected vary from cycle to cycle because initial drain volume $V_{D0}$ varies from cycle to cycle. Initial drain volume $V_{D0}$ varies from cycle to cycle because residual volume (volume remaining in the patient's peritoneum after drain is completed) varies from cycle to cycle. As seen in FIG. 6B, residual volume jumps from 150 ml after cycle 1 to 537 ml for cycle 2 and then increases more slowly to 631 ml and 654 ml for cycles three and four.

Figure 7:
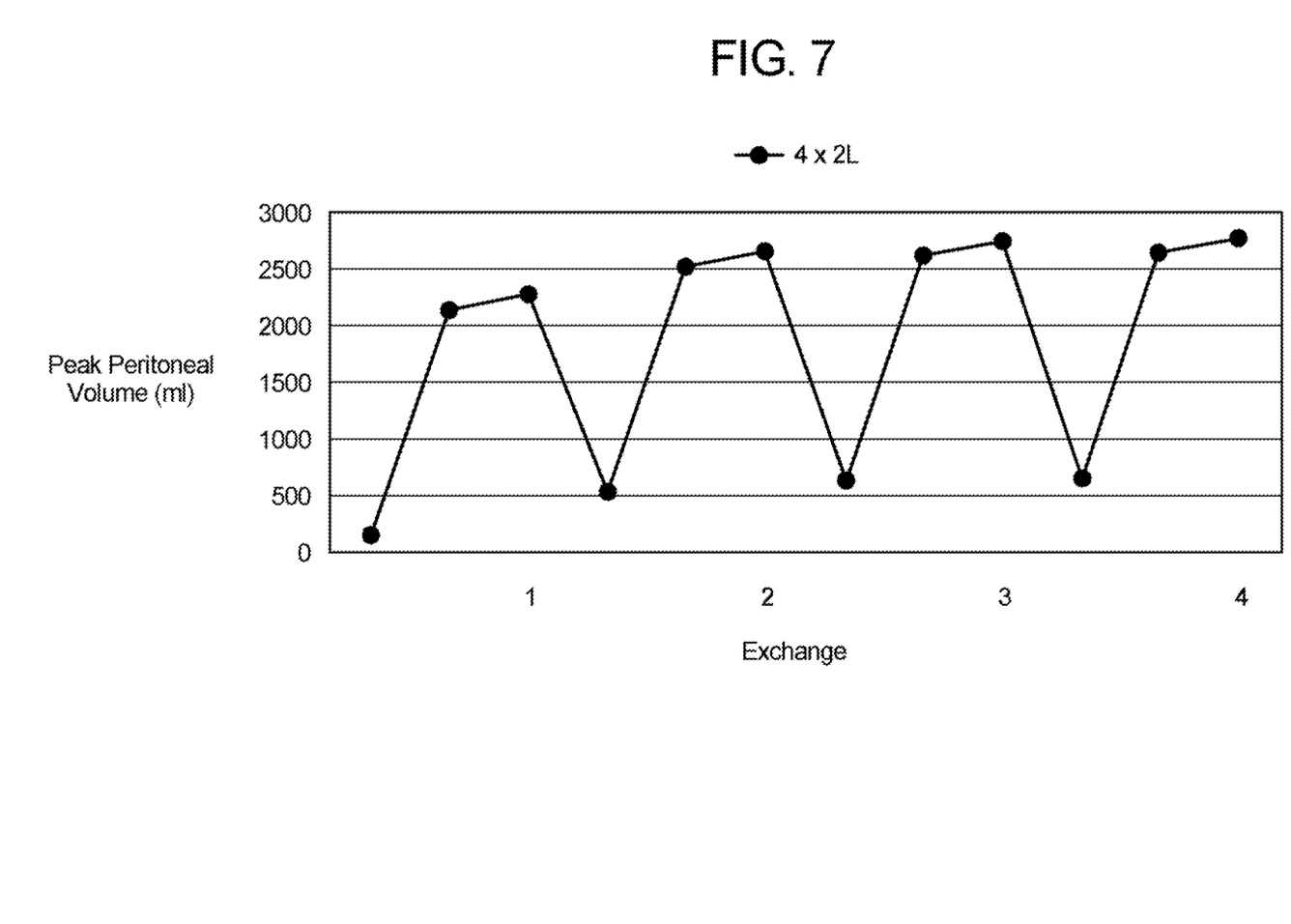
FIG. 7 is a graph illustrating peritoneal volume over time for the therapy illustrated in FIGS. 6A to 6C.

FIG. 6C shows the three-pore kinetic model's predicted UF removed for the therapy of FIG. 6B. FIG. 6B and FIG. 7 (graphing peak volume over the cycles) highlight one concern about the "four exchange each of a two liter fill" therapy of FIG. 6B, namely, that the predicted peak volume of the patient indicates the patient may become overfilled. A peak volume of roughly 2700 ml may be too high for many patients.

Figure 8A:
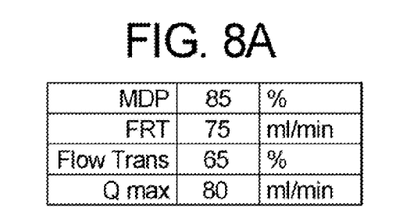
FIGS. 8A to 8C illustrate a second therapy modeled via kinetic model using information obtained from the drain volume modeling method and apparatus of the present disclosure.
Figure 8B:
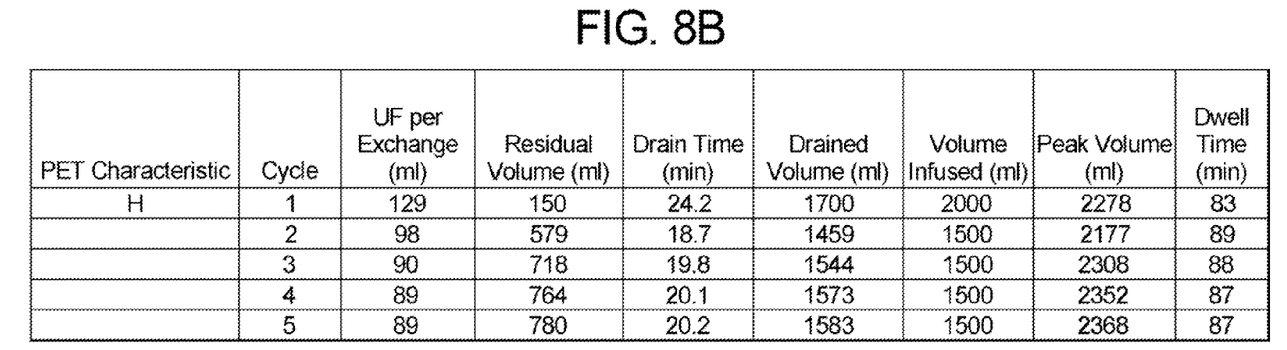
Figure 8C:
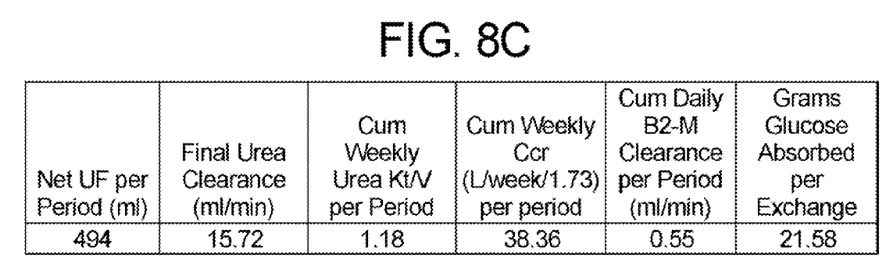

Referring now to FIGS. 8A to 8C, a second example therapy modeled using a three-pore kinetic model is illustrated. The three-pore kinetic model again used drain times selected from drain volume and drain flowrate profiles, similar to FIGS. 3 and 4, calculated via the equation above. Here, instead of four exchanges of two liter fills each, the patient undergoes a first exchange using a two liter fill, and then four exchanges each of a 1.5 liter fill, totaling eight liters like above. PET characteristic is again high.

A modeled drain time and corresponding drain volume is shown for each cycle in FIG. 8B. In each case, the drain volume met the MDP requirement of 85% and the minimum drain flowrate met the FRT requirement of 75 ml/min shown in FIG. 8A. FIG. 8A also shows patient specific parameters of an FTP of 65% and a $Q_{max}$ of 80 ml/min. As seen in FIG. 8B, the drain time and drain volume vary from cycle to cycle because initial drain volume $V_{D0}$ varies from cycle to cycle. Here, the first drain volume is the biggest and the first drain time is the longest because the first fill is the biggest, namely, two liters versus 1.5 liters for the remaining four fills. The drain volumes and drain times increase from cycle two to cycle five because residual volume increases in each instance from cycle two to cycle five.

Figure 9:
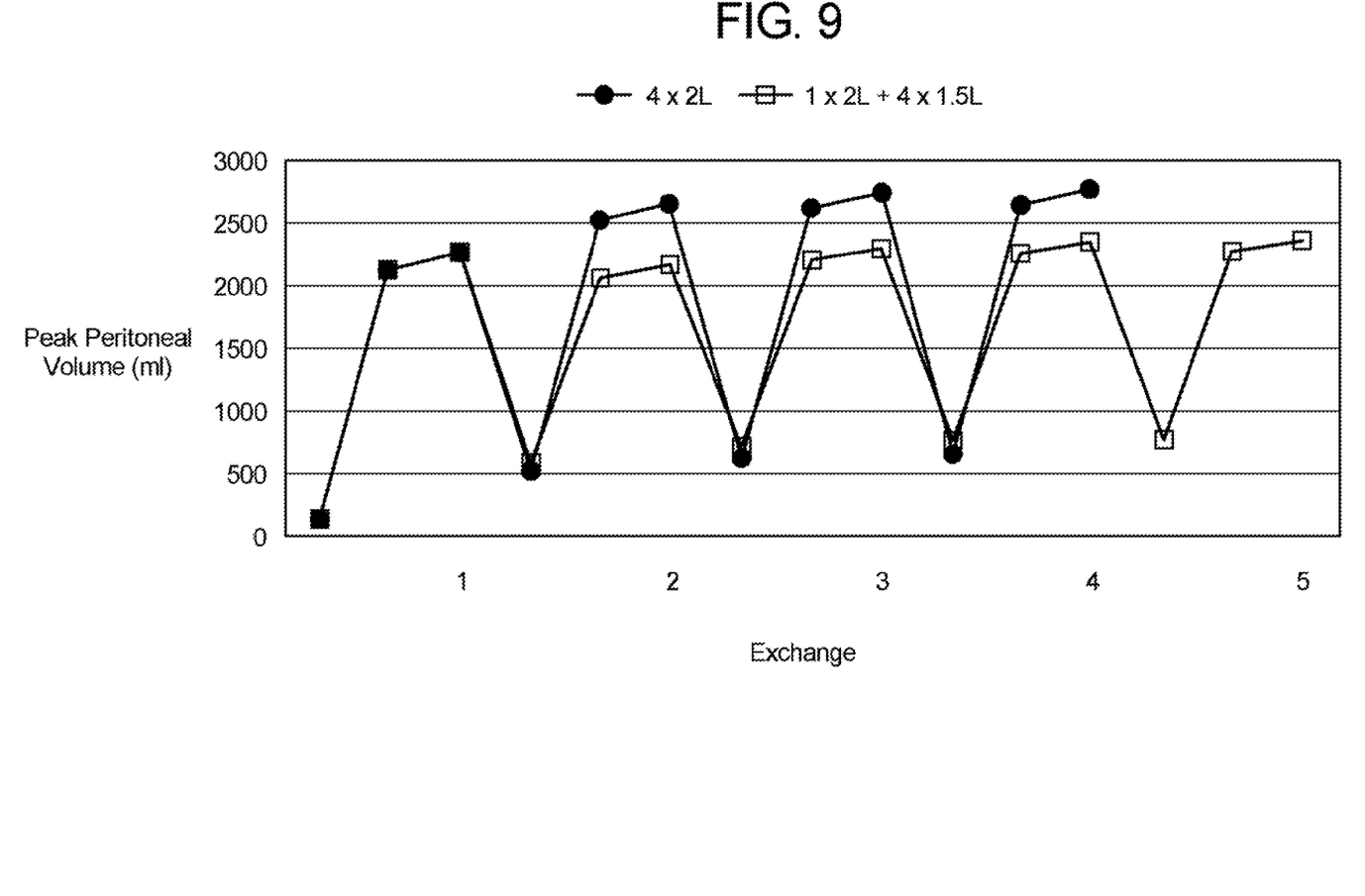
FIG. 9 is a graph illustrating peritoneal volume over time for the therapy illustrated in FIGS. 8A to 8C.

FIGS. 8B and 9 highlight that five exchange or cycle therapy of FIG. 8B predicts a reduction of the maximum peak volume to roughly 2350 ml, which may be better suited for the particular patient. FIG. 8C shows the three-pore kinetic model's predicted UF removed for the therapy of FIG. 8B. The UF removed and overall clearances are comparable to those of FIG. 6C, and the patient absorbs less glucose, which is beneficial because the patient does not gain as much weight. Thus, assuming that the additional exchange can be done in a prescribed or desired total therapy duration, the therapy of FIG. 8B may be more desirable than the therapy of FIG. 6B. In any case, the more accurately predicted drain times and volumes discussed herein allow the therapies of FIGS. 6B and 8B to be predicted more accurately, so that a better and more informed decision can be made for the patient.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of modeling a patient's peritoneal dialysis drain phase comprising:
    determining a constant flowrate for the patient residing in a particular patient position;
    modeling a first segment of a drain phase curve as having the constant flowrate;
    modeling a second segment of a drain phase curve as having a decaying exponential flowrate;
    incorporating a switching component into the first and second segments so that (i) at a first time the first segment is active while the second segment is inactive and (ii) at a second time the first segment is inactive while the second segment is active; and
    programming a computer to use the modeled first and second drain phase segments for at least one of: (i) determining a drain time for an automated peritoneal dialysis ("APD") machine, (ii) determining a dwell time for the APD machine, (iii) determining a drain time for a continuous ambulatory peritoneal dialysis therapy, (iv) setting a low flowrate alarm in the APD machine, (v) setting a minimum drain volume percentage in the APD machine, (vi) determining a dwell time for use in kinetically modeling a patient, and (vii) preventing overfilling of the patient.

2. The method of claim 1, which includes determining the constant flowrate empirically.

3. The method of claim 1, wherein the particular patient position is one of standing, sitting or lying down.

4. The method of claim 1, which includes determining a time of transition from the first segment to the second segment for the switching component empirically.

5. The method of claim 1, which includes a patient specific constant used with the decaying exponential flowrate empirically.

6. The method of claim 1, which includes entering at least one of the drain time, dwell time and low flowrate alarm setting into the APD machine.

7. The method of claim 6, wherein the APD machine uses gravity for drain or pumps to drain.

8. The method of claim 1, which includes using the model to ensure that the drain flowrate does not fall below a certain level during therapy.

9. A model of a patient's peritoneal dialysis drain phase produced via the method of claim 1.

10. A method of modeling a patient's peritoneal dialysis drain phase comprising:
    modeling a first segment of a drain phase curve as having a linear decrease in drain volume from the patient residing in a particular patient position;
    modeling a second segment of a drain phase curve as having an exponentially decaying decrease in drain volume from the patient;
    incorporating a switching component into the first and second segments so that (i) at a first time the first segment is active while the second segment is inactive and (ii) at a second time the first segment is inactive while the second segment is active; and
    programming a computer to use the modeled first and second drain phase segments for at least one of: (i) determining a drain time for an automated peritoneal dialysis ("APD") machine, (ii) determining a dwell time for the APD machine, (iii) determining a drain time for a continuous ambulatory peritoneal dialysis therapy, (iv) setting a low flowrate alarm in the APD machine, (v) setting a minimum drain volume percentage in the APD machine, (vi) determining a dwell time for use in kinetically modeling a patient, (vii) preventing overfilling of the patient, and (viii) determining a time at which the patient's drain volume is calculated to drop to a certain level as a drain phase duration for therapy.

11. The method of claim 10, which includes entering the time at which the patient's drain volume is calculated to drop to a certain level as a drain phase duration for therapy into the APD machine.

12. The method of claim 10, which includes using the method to ensure that the certain level of drain volume removed over the drain phase duration is below a minimum drain volume level or percentage.

13. The method of claim 10, which includes using the method to ensure that the drain phase flowrate does not fall below a minimum level over the drain phase duration.

14. The method of claim 10, wherein the particular patient position is one of standing, sitting or lying down.

15. An apparatus for modeling a patient's peritoneal dialysis drain phase comprising:

a computer; and a non-transitory computer readable medium modified to yield an instantaneous drain volume remaining in a patient, $V_D$, which is equal to $[V_{D0}-Q_{max}*t]*\Phi + [V_{D0}*e^{-\alpha t}]*(1-\Phi)$, wherein $V_{D0}$ is an initial patient drain volume;

$Q_{max}$ is a starting flowrate;

$\Phi$ is a switching component;

$\alpha$ is a decaying exponential constant; and t is time, and wherein the computer executes the computer readable medium and outputs the instantaneous drain volume.

16. The apparatus of claim 15, wherein $V_{D0}$ is estimated from a fill volume plus an expected amount of ultrafiltrate removed from the patient over a previous dwell phase.

17. The apparatus of claim 15, wherein $Q_{max}$ is at least one of (i) patient specific, (ii) patient drain position specific, and (iii) determined empirically.

18. The apparatus of claim 15, wherein $\Phi$ is either 1 or 0 depending on time t.

19. The apparatus of claim 18, wherein $\Phi$ switches from 1 to 0 at a time t or a volume $V_D$ that is determined empirically.

20. The apparatus of claim 15, wherein $\alpha$ is at least one of (i) patient specific and (iii) determined empirically.

21. The apparatus of claim 15, wherein the computer readable medium is further modified to use $V_D$ to at least one of: (i) determine a drain time for an automated peritoneal dialysis ("APD") machine; (ii) determine a dwell time for the automated peritoneal dialysis ("APD") machine; (iii) determine a drain time for a continuous ambulatory peritoneal dialysis therapy; (iv) set a low flowrate alarm in an APD machine; (v) set a minimum drain volume percentage in the APD machine; (vi) determine a dwell time for use in kinetically modeling a patient; and (vii) prevent overfilling of the patient.

* * * * *